(12) United States Patent
Geisser et al.

(10) Patent No.: US 7,612,109 B2
(45) Date of Patent: Nov. 3, 2009

(54) WATER-SOLUBLE IRON-CARBOHYDRATE COMPLEXES, PRODUCTION THEREOF, AND MEDICAMENTS CONTAINING SAID COMPLEXES

(75) Inventors: Peter Geisser, St. Gallen (CH); Erik Philipp, Wittenbach (CH); Walter Richle, Gossau (CH)

(73) Assignee: Vifor (International) AG, St. Gallen (CH)

( * ) Notice: Subject to any disclaimer, the term of this patent is extended or adjusted under 35 U.S.C. 154(b) by 108 days.

(21) Appl. No.: 10/531,895

(22) PCT Filed: Oct. 20, 2003

(86) PCT No.: PCT/EP03/11596

§ 371 (c)(1),
(2), (4) Date: Dec. 14, 2005

(87) PCT Pub. No.: WO2004/037865

PCT Pub. Date: May 6, 2004

(65) Prior Publication Data

US 2006/0205691 A1    Sep. 14, 2006

(30) Foreign Application Priority Data

Oct. 23, 2002  (DE) ................. 102 49 552

(51) Int. Cl.
*A61K 31/295*  (2006.01)
*A61K 31/721*  (2006.01)
*A61K 47/36*   (2006.01)
*A61P 7/06*    (2006.01)

(52) U.S. Cl. .......................... 514/502; 514/58; 514/59; 514/777; 514/814

(58) Field of Classification Search .................. 514/502, 514/54, 58, 59, 777
See application file for complete search history.

(56) References Cited

U.S. PATENT DOCUMENTS

| 3,086,009 A | 4/1963 | Zuschek et al. |
| 3,821,192 A | 6/1974 | Montgomery et al. |
| 5,746,999 A | 5/1998 | Gries et al. |
| 5,831,043 A * | 11/1998 | Fleche ................. 536/18.5 |

FOREIGN PATENT DOCUMENTS

| FR | 1451203 | 1/1966 |
| GB | 1111929 | 5/1968 |
| WO | 02/46241 | 6/2002 |

OTHER PUBLICATIONS

HCAPLUS abstract 1960:117732 (1960).*
HCAPLUS abstract 2003:135397; abstracting CN 1353194 (abstract publicly available on Feb. 24, 2003).*
Thaburet, J.F. et al., "Tempo-mediated oxidation of maltrodextrins and D-glucose . . . " Carbohydrate Research, vol. 330, pp. 21-29 (2001).*
Dokic, P. et al., "Molecular characteristics of maltodextrins and rheological behaviour of diluted and concentrated solutions," Colloids and Surfaces, vol. 141, pp. 435-440 (1998).*
English translation of CN 1353194 (Jun. 12, 2002).*
International Search Report for PCT/EP03/11596 dated Jan. 14, 2004, four pages.

* cited by examiner

*Primary Examiner*—John Pak
(74) *Attorney, Agent, or Firm*—Rankin, Hill & Clark LLP

(57) ABSTRACT

Water soluble iron carbohydrate complex obtainable from an aqueous solution of iron (III) salt and an aqueous solution of the oxidation product of one or more maltrodextrins using an aqueous hypochlorite solution at a pH-value within the alkaline range, where, when one maltodextrin is applied, its dextrose equivalent lies between 5 and 20, and when a mixture of several maltodextrins is applied, the dextrose equivalent of the mixture lies between 5 and 20 and the dextrose equivalent of each individual maltodextrin contained in the mixture lies between 2 and 40, process for its production and medicament for the treatment and prophylaxis of iron deficiency conditions.

27 Claims, No Drawings

WATER-SOLUBLE IRON-CARBOHYDRATE COMPLEXES, PRODUCTION THEREOF, AND MEDICAMENTS CONTAINING SAID COMPLEXES

This application is a 35 U.S.C. section 371 filing of PCT/EP2003/011596, filed on Oct. 20, 2003, and published May 6, 2004 as WO 2004/037865 A1, which claims priority to German Patent Application DE 10249552.1, filed Oct. 23, 2002. The foregoing documents are incorporated herein by reference.

The present invention concerns water-soluble iron carbohydrate complexes which are used for the treatment of iron deficiency anaemia, their preparation, medicaments containing them and their use for the prophylaxis or treatment of iron deficiency anaemia. The medicaments are especially useful for parenteral application.

Iron deficiency anaemia can be treated or prophylactically treated by the application of medicaments containing iron. In this respect the use of iron carbohydrate complexes is known. A water soluble iron (III) hydroxide sucrose complex is a frequently and successfully used preparation (Danielson, Salmonson, Derendorf, Geisser, Drug Res., Vol. 46: 615-621, 1996). It is also known in the art to use, for parenteral application, iron dextran complexes as well as complexes based on pullulans (WO 02/46241), which are difficult to obtain and have to be produced under pressure at high temperatures and involving hydrogenating steps. Other iron carbohydrate complexes are also known for oral application.

The problem to be solved by the present invention is to provide an iron preparation which is especially to be applied parenterally and which can easily be sterilized; the known parenterally applicable preparations on the basis of sucrose and dextran were only stable at temperatures up to 100° C., which made sterilisation difficult. Further, the preparation to be provided by the invention shall have reduced toxicity and shall avoid dangerous anaphylactic shocks which can be induced by dextran. Also, the stability of the complexes of the preparation shall be high in order to enable a high applicable dosage and a high rate of application. Furthermore, the iron preparation is to be producible from easily obtainable starting products and without great effort.

In accordance with the present invention the problem can be solved by providing iron (III) carbohydrate complexes on the basis of the oxidation products of maltodextrins. Therefore, an object of the present invention are water soluble iron carbohydrate complexes which are obtainable from an aqueous solution of an iron (III) salt and an aqueous solution of the oxidation product of one or more maltodextrins, using an aqueous hypochlorite solution at an alkaline pH-value of e.g. 8 to 12 where, when one maltodextrin is applied, its dextrose equivalent lies between 5 and 20, and when a mixture of several maltodextrins is applied, the dextrose equivalent of the mixture lies between 5 and 20 and the dextrose equivalent of each individual maltodextrin contained in the mixture lies between 2 and 40.

A further object of the present invention is a process for producing the iron carbohydrate complexes according to the invention wherein one or more maltodextrins are oxidized in an aqueous solution at an alkaline pH-value of e.g. 8 to 12 using an aqueous hypochlorite solution and reacting the obtained solution with an aqueous solution of an iron (III) salt where, when one maltodextrin is applied, its dextrose equivalent lies between 5 and 20, and when a mixture of several maltodextrins is applied, the dextrose equivalent of the mixture lies between 5 and 20 and the dextrose equivalent of each individual maltodextrin contained in the mixture lies between 2 and 40.

The usable maltodextrins are easily obtainable starting products, and they are commercially available.

In order to prepare the ligands of the complexes of the invention, the maltodextrins are oxidized in an aqueous solution with a hypochlorite solution. Suitable examples are solutions of alkali hypochlorites such as a solution of sodium hypochlorite. Commercially available solutions can be used. The concentration of the hypochlorite solution is, e.g. at least 13% by weight, preferably in the order of 13 to 16% by weight, calculated as active chlorine. Preferably the solutions are used in such an amount that about 80 to 100%, preferably about 90% of one aldehyde group per molecule of maltodextrin is oxidized. In this manner, the reactivity caused by the glucose content of the maltodextrin molecules is lowered to 20% or less, preferably to 10% or less.

The oxidation is carried out in an alkaline solution, e.g. at a pH of 8 to 12, for example 9 to 11. As an example, oxidation can be carried out at temperatures in the order of 15 to 40° C., preferably of 25 to 35° C. The reaction times are, e.g. in the order of 10 minutes to 4 hours, e.g. 1 to 1.5 hours.

By this procedure the degree of depolymerisation of the starting maltodextrins is kept at a minimum. Only theoretically it is assumed that the oxidation occurs mainly at the terminal aldehyde group (acetal or semiacetal group respectively) of the maltodextrin molecules.

It is also possible to catalyse the oxidation reaction of the maltodextrins. The addition of bromide ions is suitable, e.g. in the form of alkali bromides, for example sodium bromide. The added amount of bromide is not critical. The amount is kept as low as possible in order to achieve an end product (Fe-complex) which can easily be purified. Catalytic amounts are sufficient. As stated above, the addition of bromide is possible, however, not necessary.

Further, it is also possible to use other oxidation systems, such as e.g. the known ternary oxidation system hypochlorite/alkali bromide/2,2,6,6,-tetramethypiperidine-1-oxyl (TEMPO) for the oxidation of the maltodextrins. The process to oxidize maltodextrins catalytically with alkali bromides or with the ternary TEMPO system is described e.g. by Thaburet et al in Carbohydrate Research 330 (2001) 21-29, which method can be used for the present invention.

In order to prepare the complexes of the invention the obtained oxidized maltodextrins are reacted with an iron (III) salt in an aqueous solution. In order to do so, the oxidized maltodextrins can be isolated and redissolved; however, it is also possible to use the obtained aqueous solutions of the oxidized maltodextrins directly for the further reaction with the aqueous iron (III) solutions.

Water soluble salts of inorganic or organic acids, or mixtures thereof, such as halides, e.g. chloride and bromide or sulfates can be used as iron (III) salts. It is preferred to use physiologically acceptable salts. It is especially preferred to use an aqueous solution of iron (III) chloride.

It has been found that the presence of chloride ions favours the formation of the complexes. The chloride ions can be used in the form of water soluble chlorides such as alkali metal chlorides, e.g. sodium chloride, potassium chloride or ammonium chloride. As stated, the iron (III) is preferably used in the form of the chloride.

For instance, the aqueous solution of the oxidized maltodextrin can be mixed with an aqueous solution of the iron (III) salt in order to carry out the reaction. Here, it is preferred to proceed in a manner so that during and immediately after mixing of the oxidized maltodextrin and the iron (III) salt, the pH is strongly acid or so low that no hydrolysis of the iron (III) salt occurs, e.g. 2 or less, in order to avoid an undesired precipitation of iron hydroxides. In general, it is not necessary to add an acid, if iron (III) chloride is used, since aqueous solutions of iron (III) chloride can be sufficiently acid. Only after mixing, the pH is raised to values of e.g. in the order of at least 5, for example up to 11, 12, 13 or 14. The pH is preferably raised slowly or gradually which, for example, can be achieved by first adding a weak base, for example, up to a pH of about 3, and then neutralizing further using a stronger base. Examples of weak bases are alkali- or alkaline earth-carbonates, bicarbonates, such as sodium and potassium carbonate or bicarbonate, or ammonia. Examples of strong bases are alkali- or alkaline earth-hydroxides such as sodium, potassium, calcium or magnesium hydroxide.

The reaction can be improved by heating. For example, temperatures in the order of 15° C. up to boiling point can be used, It is preferred to raise the temperature gradually. Thus, for example, it is possible to heat to about 15 to 70° C. and then raise the temperature gradually up to boiling point.

The reaction times are, for example, in the order of 15 minutes up to several hours, e.g. 20 minutes to 4 hours, such as 25 to 70 minutes, e.g. 30 to 60 minutes.

The reaction can be carried out in a weakly acid range, for example, at a pH in the order of 5 to 6. However, it has been found, that it is useful, but not necessary, to raise the pH during the formation of the complexes to higher values of up to 11, 12, 13 or 14. In order to complete the reaction, the pH can be lowered then by addition of an acid, for example, to the order of 5 to 6. It is possible to use inorganic or organic acids or mixture thereof, especially hydrogen halide acids such as hydrogen chloride or aqueous hydrochloric acid respectively.

As stated above, the formation of the complexes is usually improved by heating. Thus, at the preferred embodiment of the invention, wherein the pH is raised during the reaction to ranges of at least 5 and above up to 11 or 14, it is, for instance, possible to work at first at lower temperatures in the order of 15 to 70° C., such as 40 to 60° C., e.g. about 50° C., whereafter the pH is reduced to values in the order of at least 5 and the temperature is gradually raised over 50° C. up to boiling point.

The reaction times are in the order of 15 minutes up to several hours and they can vary depending on the reaction temperature. If the process is carried out with an intermediate pH of more than 5, it is, for example, possible to work 15 to 70 minutes, e.g. 30 to 60 minutes, at the enhanced pH, for example at temperatures of up to 70° C., whereafter the pH is lowered to a range in the order of at least 5 and the reaction is carried out for a further 15 to 70 minutes, e.g. 30 to 60 minutes, at temperatures e.g. up to 70° C., and optionally a further 15 to 70 minutes, e.g. 30 to 60 minutes, at higher temperatures up to boiling point.

After the reaction the obtained solution can be cooled to e.g. room temperature and can optionally be diluted and optionally be filtered. After cooling, the pH can be adjusted to the neutral point or a little below, for example, to values of 5 to 7, by the addition of an acid or base. It is possible to use e.g. the acids and bases which have been mentioned for carrying out the reaction. The solutions obtained are purified and can directly be used for the production of medicaments. However, it is also possible to isolate the iron (III) complexes from the solution e.g. by precipitation with an alcohol such as an alkanol, for example, ethanol. Isolation can also be effected by spray-drying. Purification can take place in the usual way, especially in order to remove salts. This can, for example, be carried out by reverse osmosis. It is, for example, possible to carry out the reverse osmosis before spray-drying or before a direct application in medicaments.

The iron content of the obtained iron (III) carbohydrate complexes is, for example, 10 to 40% weight/weight, especially, 20 to 35% weight/weight. They can easily be dissolved in water. It is possible to prepare neutral aqueous solutions which, e.g. have an iron content of 1% weight/vol. to 20% weight/vol. Such solutions can be sterilised thermally. The weight average molecular weight mw of the obtained complexes, is, for example, 80 kDa to 400 kDa, preferably 80 kDa to 350 kDa, especially preferred up to 300 kDa (measured by gel permeation chromatography, e.g. as described by Geisser et al, in Arzneim. Forsch/Drug Res. 42(II), 12, 1439-1452 (1992), paragraph 2.2.5).

As stated above, it is possible to provide aqueous solutions from the complexes of the invention. These solutions are especially useful for parenteral application. However, it is also possible to apply them orally or topically. Contrary to the known parenterally applicable iron preparations they can be sterilized at high temperatures, e.g. at 121° C. and above, at short contact times of, e.g. 15 minutes, by acquiring $F_0 \geq 15$. The contact times are correspondingly shorter at higher temperatures. Preparations hitherto known had to be sterilely filtrated and mixed with preservatives, such as benzyl alcohol or phenol. Such additives are not necessary in the invention. Hence, it is possible to fill the solutions of the complexes, for example, into ampoules. It is, for example, possible, to fill solutions having a content of 1 to 20% by weight, e.g. 5% by weight, into vessels such as ampoules or phials of e.g. 2 to 100 ml, e.g., up to 50 ml. The preparation of the parenterally applicable solutions can be carried out as known in the art, optionally using additives which are normally used for parenteral solutions. The solutions can be formulated in such a way that they can be administered by injection or in the form of an infusion, e.g., in brine solution. For the oral or topical application it is possible to formulate preparations with usual excipients and additives.

Thus, a further object of the invention are aqueous medicaments which are especially useful for the parenteral, intravenous but also intramuscular application as well as for the oral or topical application; they are especially useful for the treatment of iron deficiency anaemia. A further object of the invention is also the use of the iron (III) carbohydrate complexes according to the invention for the treatment and prophylaxis of iron deficiency anaemia or the production of medicaments especially for the parenteral treatment iron deficiency anaemia. The medicaments can be used in human and veterinary medicine.

The advantages which are achieved with the iron (III) carbohydrate complexes of the invention are the above-mentioned high sterilisation temperatures as well as the low toxicity and the reduced danger of anaphylactic shock. The toxicity of the complexes according to the invention is very low. The $LD_{50}$ lies at over 2000 mg Fe/kg, compared to the $LD_{50}$ of the known pullulan complexes, which lies at 1400 mg Fe/kg. In view of the high stability of the complexes of the invention, it is possible to enhance the rates of application as well as the dosages. Thus, it is possible to apply the medicaments of the invention parenterally in the form of a single dose. Such a single dose is, for example, 500 to 1000 mg iron; it can be applied, for example, during the course of one hour. A further advantage lies in the high degree of availability of the maltodextrins used as starting products, which are, e.g., commercially available additives in the food processing industry.

In the present description, as well as in the following examples, the dextrose equivalents are measured gravimetrically. In order to do so, the maltodextrins are reacted in a boiling aqueous solution with Fehling's solution. The reaction is carried out quantitatively, i.e. until the Fehling's solution is no longer discoloured. The precipitated copper (I) oxide is dried at 105° C. until a constant weight is achieved and measured gravimetrically. The glucose content (dextrose equivalent) is calculated from the obtained results as % weight/weight of the maltodextrin dry substance. It is, for example, possible to use the following solutions: 25 ml Fehling's solution I, mixed with 25 ml Fehling's solution II; 10 ml aqueous maltodextrin solution (10% mol/vol) (Fehling's solution I: 34.6 g copper (II) sulfate dissolved in 500 ml water; Fehling's solution II: 173 g potassium sodium tartrate and 50 g sodium hydroxide dissolved in 400 ml water).

EXAMPLE 1

100 g maltodextrin (9.6 dextrose equivalent measured gravimetrically) are dissolved by stirring in 300 ml water at 25° C. and oxidized by addition of 30 g sodium hypochlorite solution (13 to 16 weight percent active chlorine) at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide and the solution is heated to 50° C. and kept at 50° C. for 30 minutes. Then, acidification to a pH of 5 to 6 is effected by addition of hydrochloric acid, the solution is kept at 50° C. for a further 30 minutes and then heated to 97-98° C. and the temperature is kept for 30 minutes at this range. After cooling the solution to room temperature, the pH is adjusted to 6-7 by the addition of sodium hydroxide.

The solution is then-filtered through a sterilisation filter and then examined for sediments. Thereafter, the complex is isolated by precipitation with ethanol in a range of 1:0.85 and then dried in vacuum at 50° C.

The yield is 125 g (corresponding to 87% of the theoretical value) of a brown amorphous powder having an iron content of 29,3% weight/weight (measured complexometrically).

Molecular weight mw 271 kDa.

EXAMPLE 2

200 g maltodextrin (9.6 dextrose equivalent measured gravimetrically) are dissolved by stirring in 300 ml water at 25° C. and oxidized by addition of 30 g sodium hypochlorite solution (13 to 16 weight percent active chlorine) at pH 10.

At first the oxidized maltodextrin solution and then 554 g sodium carbonate solution (17.3% weight/weight) are added at room temperature to 352 g of a stirred iron (III) chloride solution (12% weight by weight Fe).

Then the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 30 minutes and then heated to 97-98° C. and the temperature is kept for 30 minutes at this range. After cooling the solution to room temperature the pH is adjusted to 6-7 by the addition of sodium hydroxide.

The solution is then filtered through a sterilisation filter and then examined for sediments. Thereafter, the complex is isolated by precipitation with ethanol in a range of 1:0.85 and then dried in vacuum at 50° C.

The yield is 123 g (corresponding to 65% of the theoretical value) of a brown amorphous powder having an iron content of 22.5% weight/weight (measured complexometrically).

Molecular weight mw 141 kDa.

EXAMPLE 3

100 g maltodextrin (9.6 dextrose equivalent measured gravimetrically) are dissolved by stirring in 300 ml water at 25° C. and oxidized by addition of 30 g sodium hypochlorite solution (13 to 16 weight percent active chlorine) and 0.7 g sodium bromide at pH 10.

At first the oxidized maltodextrin solution and then 554 g sodium carbonate solution (17.3% weight/weight) are added at room temperature to 352 g of a stirred iron (III) chloride solution (12% weight by weight Fe).

Then the pH is adjusted to 6.5 by addition of sodium hydroxide and the solution is heated to 50° C. and kept for 60 minutes at 50° C. Then, acidification to a pH of 5 to 6 is effected by addition of hydrochloric acid, the solution is kept at 50° C. for a further 30 minutes and then heated to 97-98° C. and the temperature is kept for 30 minutes at this range. After cooling the solution to room temperature the pH is adjusted to 6-7 by the addition of sodium hydroxide.

The solution is then filtered through a sterilisation filter and then examined for sediments. Thereafter, the complex is isolated by precipitation with ethanol in a range of 1:0.85 and then dried in vacuum at 50° C.

The yield is 139 g (corresponding to 88% of the theoretical value) of a brown amorphous powder having an iron content of 26.8% weight/weight (measured complexometrically).

Molecular weight mw 140 kDa.

EXAMPLE 4

A mixture of 45 g maltodextrin (6.6 dextrose equivalent measured gravimetrically) and 45 g maltodextrin (14.0 dextrose equivalent measured gravimetrically) is dissolved by stirring in 300 ml water at 25° C. and oxidized by addition of 25 g sodium hypochlorite solution (13 to 16 weight percent active chlorine) and 0.6 g sodium bromide at pH 10.

At first the oxidized maltodextrin solution and then 554 g sodium carbonate solution (17.3% weight/weight) are added at room temperature to 352 g of a stirred iron (III) chloride solution (12% weight by weight Fe).

Then the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 30 minutes and then heated to 97-98° C. and the temperature is kept for 30 minutes at this range. After cooling the solution to room temperature the pH is adjusted to 6-7 by the addition of sodium hydroxide.

The solution is then filtered through a sterilisation filter and then examined for sediments. Thereafter, the complex is isolated by precipitation with ethanol in a range of 1:0.85 and then dried in vacuum at 50° C.

The yield is 143 g (corresponding to 90% of the theoretical value) of a brown amorphous powder having an iron content of 26.5% weight/weight (measured complexometrically).

Molecular weight mw 189 kDa.

EXAMPLE 5

90 g maltodextrin (14.0 dextrose equivalent measured gravimetrically) are dissolved by stirring in 300 ml water at 25° C. and oxidized by addition of 35 g sodium hypochlorite solution (13 to 16 weight percent active chlorine) and 0.6 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 30 minutes and then heated to 97-98° C. and the temperature is kept for 30 minutes at this range. After cooling the solution to room temperature the pH is adjusted to 6-7 by the addition of sodium hydroxide.

The solution is then filtered through a sterilisation filter and then examined for sediments. Thereafter, the complex is isolated by precipitation with ethanol in a range of 1:0.85 and then dried in vacuum at 50° C.

The yield is 131 g (corresponding to 93% of the theoretical value) of a brown amorphous powder having an iron content of 29.9% weight/weight (measured complexometrically).

Molecular weight mw 118 kDa.

EXAMPLE 6

A mixture of 45 g maltodextrin (5.4 dextrose equivalent measured gravimetrically) and 45 g maltodextrin (18.1 dextrose equivalent measured gravimetrically) is dissolved by stirring in 300 ml water at 25° C. and oxidized by addition of 31 g sodium hypochlorite solution (13 to 16 weight percent active chlorine) and 0.7 g sodium bromide at pH 10.

At first the oxidized maltodextrin solution and then 554 g sodium carbonate solution (17.3% weight/weight) are added at room temperature to 352 g of a stirred iron (III) chloride solution (12% weight by weight Fe).

Then the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 30 minutes and then heated to 97-98° C. and the temperature is kept for 30 minutes at this range. After cooling the solution to room temperature the pH is adjusted to 6-7 by the addition of sodium hydroxide.

The solution is then filtered through a sterilisation filter and then examined for sediments. Thereafter, the complex is isolated by precipitation with ethanol in a range of 1:0.85 and then dried in vacuum at 50° C.

The yield is 134 g (corresponding to 88% of the theoretical value) of a brown amorphous powder having an iron content of 27.9% weight/weight (measured complexometrically).

Molecular weight mw 178 kDa.

EXAMPLE 7

100 g maltodextrin (9.6 dextrose equivalent measured gravimetrically) are dissolved by stirring in 300 ml water at 25° C. and oxidized by addition of 29 g sodium hypochlorite solution (13 to 16 weight percent active chlorine) and 0.7 g sodium bromide at pH 10.

At first the oxidized maltodextrin solution and then 554 g sodium carbonate solution (17.3% weight/weight) are added at room temperature to 352 g of a stirred iron (III) chloride solution (12% weight by weight Fe).

Then the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 70 minutes. After cooling the solution to room temperature the pH is adjusted to 6-7 by the addition of sodium hydroxide.

The solution is then filtered through a sterilisation filter and then examined for sediments. Thereafter, the complex is isolated by precipitation with ethanol in a range of 1:0.85 and then dried in vacuum at 50° C.

The yield is 155 g (corresponding to 90% of the theoretical value) of a brown amorphous powder having an iron content of 24.5% weight/weight (measured complexometrically).

Molecular weight mw 137 kDa.

EXAMPLE 8

126 g maltodextrin (6.6 dextrose equivalent measured gravimetrically) are dissolved by stirring in 300 ml water at 25° C. and oxidized by addition of 24 g sodium hypochlorite solution (13 to 16 weight percent active chlorine) and 0.7 g sodium bromide at pH 10.

At first the oxidized maltodextrin solution and then 554 g sodium carbonate solution (17.3% weight/weight) are added at room temperature to 352 g of a stirred iron (III) chloride solution (12% weight by weight Fe).

Then the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 70 minutes. After cooling the solution to room temperature the pH is adjusted to 6-7 by the addition of sodium hydroxide.

The solution is then filtered through a sterilisation filter and then examined for sediments. Thereafter, the complex is isolated by precipitation with ethanol in a range of 1:0.85 and then dried in vacuum at 50° C.

The yield is 171 g (corresponding to 86% of the theoretical value) of a brown amorphous powder having an iron content of 21.35% weight/weight (measured complexometrically).

Molecular weight mw 170 kDa.

Comparative Test

In the following the characteristics of the iron carbohydrate complexes are compared with a commercially available iron sucrose complex. It can be seen that the iron content can be enhanced, the thermal treatment can be carried out at higher temperatures and the toxicity ($LD_{50}$) can be lowered in accordance with the invention.

|  | According to the invention | Iron hydroxide/sucrose complex |
|---|---|---|
| Fe content [%] | 5.0 | 2.0 |
| pH | 5-7 | 10.5-11.0 |
| mw [kDa][1] | 80-350 | 34-54 |
| Thermal treatment | 121° C./15' | 100° C./35' |
| $LD_{50}$ i.v., w.m. [mg Fe/kg body weight] | >2000 | >200 |

The invention claimed is:

1. A water soluble iron carbohydrate complex having a weight average molecular weight (Mw) of 80,000 to 400,000, comprising the reaction product of:
   (a) an aqueous solution of an iron (III) salt and
   (b) an aqueous solution of the oxidation product of
       (i) at least one maltodextrin and
       (ii) an aqueous hypochlorite solution at an alkaline pH, wherein, when one maltodextrin is present, the maltodextrin has a dextrose equivalent of between 5 and 20, and wherein, when a mixture of more than one maltodextrin is present, the dextrose equivalent of each individual maltodextrin is between 2 and 40, and the dextrose equivalent of the mixture is between 5 and 20.

2. A medicament comprising an aqueous solution of the iron carbohydrate complex of claim 1.

3. The medicament of claim 2, wherein the medicament is formulated for parenteral or oral application.

4. The water soluble iron carbohydrate complex of claim 1, wherein the iron carbohydrate complex has a weight average molecular weight (Mw) of 80,000 to 350,000.

5. The water soluble iron carbohydrate complex of claim 1, wherein the iron carbohydrate complex has a weight average molecular weight (Mw) of 80,000 to 300,000.

6. A process for producing a water soluble iron carbohydrate complex having a weight average molecular weight (Mw) of 80,000 to 400,000, comprising the steps of:
(a) oxidizing at least one maltodextrin in an aqueous solution at an alkaline pH with an aqueous hypochlorite solution to form an oxidized maltodextrin solution, and
(b) contacting the oxidized maltodextrin solution with an aqueous solution of an iron (III) salt, wherein,
when one maltodextrin is present, the maltodextrin has a dextrose equivalent of between 5 and 20, and wherein,
when a mixture of more than one maltodextrin is present, the dextrose equivalent of each individual maltodextrin is between 2 and 40, and the dextrose equivalent of the mixture is between 5 and 20.

7. The process of claim 6, wherein the iron (III) salt is iron (III) chloride.

8. The process of claim 7, wherein step (b) is carried out at a pH of 2 or less to form a final solution, and the process further comprises (c) raising the pH of the final solution to a value in the range of 5 to 12.

9. The process of claim 7, wherein step (b) is carried out at a temperature of from 15° C. to the boiling point for 15 minutes up to several hours.

10. The process of claim 6, wherein step (b) is carried out at a pH of 2 or less to form a final solution, and the process further comprises (c) raising the pH of the final solution to a value in the range of 5 to 12.

11. The process of claim 10, wherein step (b) is carried out at a temperature of from 15° C. to the boiling point for 15 minutes up to several hours.

12. The process of claim 6, wherein step (a) is carried out in the presence of bromide ions.

13. The process of claim 12, wherein step (b) is carried out at a temperature of from 15° C. to the boiling point for 15 minutes up to several hours.

14. The process of claim 12, wherein the iron (III) salt is iron (III) chloride.

15. The process of claim 14, wherein step (b) is carried out at a pH of 2 or less to form a final solution, and the process further comprises (c) raising the pH of the final solution to a value in the range of 5 to 12.

16. The process of claim 12, wherein step (b) is carried out at a pH of 2 or less to form a final solution, and the process further comprises (c) raising the pH of the final solution to a value in the range of 5 to 12.

17. The process of claim 6, wherein step (b) is carried out at a temperature of from 40° C. to 60° C.

18. The process of claim 6, wherein step (b) is carried out at a temperature of from 50° C. to the solution boiling point.

19. A process for producing a water soluble iron carbohydrate complex having a weight average molecular weight (Mw) of 80,000 to 400,000, comprising the steps of:
(a) oxidizing at least one maltodextrin in an aqueous solution at a pH in the range of 8 to 12 and a temperature in the range of 15 to 40° C., for 10 minutes to 4 hours with an aqueous hypochlorite solution to form an oxidized maltodextrin solution,
(b) contacting the oxidized maltodextrin solution with an aqueous solution of an iron (III) salt and
(c) raising the pH of the oxidized maltodextrin solution and iron (III) salt to a value in the range of 5 to 14, wherein,
when one maltodextrin is present, the maltodextrin has a dextrose equivalent of between 5 and 20, and wherein,
when a mixture of more than one maltodextrin is present, the dextrose equivalent of each individual maltodextrin is between 2 and 40, and the dextrose equivalent of the mixture is between 5 and 20.

20. The process of claim 19, wherein at least one of the following steps are carried out: (1) step (a) is carried out at a pH in the range of 9 to 11; (2) the temperature at which step (a) is carried out is in the range of 25 to 35° C.; (3) step (a) is carried out for 1 to 1.5 hours.

21. The process of claim 19, wherein (b) is carried out at a pH of 2 or less.

22. The process of claim 19, wherein in (c), the pH is raised to a value in the range of 11 to 14.

23. The process of claim 19, further comprising after (c), (d) reducing the pH of the solution to a value in the range of 5 to 6.

24. The process of claim 23, wherein, simultaneous with (c), the solution temperature is or maintained in, the range of 15 to 70° C.

25. The process of claim 23, wherein simultaneous with (d), the solution temperature, if it is not already at least 50° C., is raised to 50° C., followed by gradually raising the temperature to the solution boiling point.

26. The process of claim 25, further comprising after (d), (e) cooling the solution to room temperature.

27. The process of claim 26, further comprising after (e), (f) adjusting the pH to a value in the range of 6 to 7.

* * * * *